(12) United States Patent
Oikawa et al.

(10) Patent No.: US 9,491,443 B2
(45) Date of Patent: Nov. 8, 2016

(54) IMAGE PROCESSING METHOD AND IMAGE PROCESSING APPARATUS

(75) Inventors: Michio Oikawa, Tokyo (JP); Hanae Yoshida, Tokyo (JP); Tomohiro Nagao, Tokyo (JP); Jiangtao Gao, Beijing (CN); Yingjie Han, Beijing (CN); Xingdong Sheng, Beijing (CN)

(73) Assignee: Hitachi, Ltd., Tokyo (JP)

( * ) Notice: Subject to any disclaimer, the term of this patent is extended or adjusted under 35 U.S.C. 154(b) by 293 days.

(21) Appl. No.: 14/129,315

(22) PCT Filed: Jun. 28, 2011

(86) PCT No.: PCT/CN2011/076480
§ 371 (c)(1),
(2), (4) Date: Mar. 5, 2014

(87) PCT Pub. No.: WO2013/000120
PCT Pub. Date: Jan. 3, 2013

(65) Prior Publication Data
US 2014/0176685 A1  Jun. 26, 2014

(51) Int. Cl.
*H04N 13/04* (2006.01)
*G06T 15/08* (2011.01)

(52) U.S. Cl.
CPC ............... *H04N 13/04* (2013.01); *G06T 15/08* (2013.01)

(58) Field of Classification Search
CPC ........................... G06T 15/08; H04N 13/0488
USPC .......................................................... 348/51
See application file for complete search history.

(56) References Cited

U.S. PATENT DOCUMENTS

2003/0097057 A1   5/2003 Oshio et al.
(Continued)

FOREIGN PATENT DOCUMENTS

| JP | 2001-351093 A | 12/2001 |
|---|---|---|
| JP | 2005046207 | 2/2005 |
| JP | 2007-275277 A | 10/2007 |
| JP | 2010-508570 A | 3/2010 |

OTHER PUBLICATIONS

International Search Report in PCT/CN2011/076480, dated Mar. 22, 2012.

*Primary Examiner* — Jeremiah C Hallenbeck-Huber
*Assistant Examiner* — Mainul Hasan
(74) *Attorney, Agent, or Firm* — Mattingly & Malur, PC

(57) ABSTRACT

An image display method and an image display apparatus to solve the three-dimensional cueing confliction problem of the maximum intensity projection in the stereoscopic display method, while enabling users to select and render with emphasis the maximum intensity projection of the objects of interest, so that to realize the stereoscopic display. A three-dimensional surface which has equal distance to a sight-point is utilized as a reference surface, and the distances from all of the local maximum intensity points to this reference surface are calculated, then a weighting factor of each local maximum intensity point is calculated according to the distances and predetermined weighting function. After, the values of local maximum intensity points are adjusted according to the obtained weighting factors, and finally, the maximum intensity projection value is produced by synthesizing all of the adjusted values of the local maximum intensity points.

16 Claims, 6 Drawing Sheets

(56) References Cited

U.S. PATENT DOCUMENTS

| | | |
|---|---|---|
| 2005/0286748 A1 | 12/2005 | Yang et al. |
| 2007/0237379 A1* | 10/2007 | Haque .................. A61B 6/463 382/130 |
| 2008/0030500 A1* | 2/2008 | Krishnan ................ G06T 15/08 345/424 |
| 2009/0147074 A1* | 6/2009 | Getty ..................... A61B 6/466 348/51 |
| 2010/0053159 A1 | 3/2010 | Visser |

* cited by examiner

IMAGE PROCESSING METHOD AND IMAGE PROCESSING APPARATUS

TECHNICAL FIELD

The present invention is concerned with the field of three-dimensional image display, and more specifically, is concerned with a stereoscopic display method and apparatus for three-dimensional data. The present invention solve the problem of three-dimensional cueing confliction, which exists in the maximum intensity three-dimensional projection, while enabling users to select and render with emphasis the maximum intensity projection of the objects of interest, so that to realize the three-dimensional display.

RELATED ART

Visualization techniques are used to extract meaningful information out of large amount of basic data and present to users through the use of interactive computer graphic techniques, so that, help the users to better understand the information and make decisions quickly. Here, we focus on visualization in scientific computing, especially the three-dimensional data visualization techniques widely used in medical, geological exploration, molecular modeling, computational fluid dynamics, etc. For example, three-dimensional data visualization techniques are greatly improving the work efficiency of the radiologist, by producing computer drawings of three-dimensional medical data from a computer tomography (CT) and magnetic resonance imaging (MRI) data, with which the lesion can be quickly located for diagnosis. In addition, on the bases of this technology and by interactive operation on the data, the computer simulation surgery and planning of orthopedic surgery and radiation therapy can be realized.

Volume rendering techniques is a very important three-dimensional display technology in scientific computing visualization. It has very good display precision, so that been widely used in medical image display areas. The maximum intensity projection, as a kind of volume rendering, is a very important medical technology, used to display the object with maximum intensity value in the direction of projection. This display method is, in some cases, of a great significance. For example, in CT angiography images, the blood vessel data have higher grayscale than other soft tissues, and the blood vessels can be displayed clearly through the maximum intensity projection technique while other soft tissues are shown as the background.

With the development of three-dimensional display technology and its continuing maturity, commercial stereoscopic display devices have emerged, and are progressively growing. The stereoscopic display technology is very different from the traditional three-dimensional display technology. It is closer to the human visual system, an approximate simulation of the human visual system, and can provide a more realistic and immersive three-dimensional effect. In highly specialized area such as medical visualization that requires very high display precision, the stereoscopic display method can improve the user's understanding of complex three-dimensional data, help physicians to locate and observe the lesions more accurately, and provide a more accurate diagnosis.

The traditional three-dimensional display technology is to convert the digitized three-dimensional scene into two-dimensional images which can be displayed on the conventional display devices by utilizing projection techniques. Typical projection technology simulates interaction between light and three-dimensional data, normally considers the positional relationship between objects and the angles among the normal rays of surfaces, the light, and the line of sight, etc., and reproduces the three-dimensional scene from a particular perspective mainly through shading and blocking relationship in two-dimensional images. The information which helps us to reproduce the three-dimensional scene is called as three-dimensional cues. The stereoscopic display method adds more three-dimensional information on the conventional three-dimensional display technology, i.e., more three-dimensional cues. It adds an additional sight-point to simulate the human visual system. Therefore, in the stereoscopic display system, two sight-points are used to simulate the left and right eyes of human being, the left and right eye-sight images are rendered separately utilizing the conventional three-dimensional display technology in computers, then, these two two-dimensional images are delivered to the left and right eyes of human beings through the stereoscopic display apparatus, just the same as the human visual system that allows the viewer to simultaneously receive two different left and right images, the human visual system will automatically handles left and right eye-sight images, so that more information about three-dimensional space and more realistic three-dimensional effects can be obtained.

Stereoscopic display method provides us with a very important three-dimensional cue, the parallax. Briefly speaking, parallax is the position difference of the same object of a three-dimensional scene in left and right eye-sight projection images. This parallax reflects the distance of the object from the two sight-points, the greater the parallax is, the farther away the object is from the two sight-points, and vice versa. Human brains can automatically obtain the information from left and right eye-sight images, so that can more accurately and more realistically reproduce three-dimensional spatial information from the three-dimensional digital data.

It is very easy to extend the traditional volume rendering technology into the stereoscopic volume rendering technology, by simply adding an additional sight-point, rendering the left and right eye-sight images, and displaying them through a stereoscopic display device. However, there is an inherent problem in the maximum intensity projection under the stereoscopic display technology, i.e., three-dimensional cueing confliction. Briefly speaking, the three-dimensional cueing confliction means that there are inconsistencies among the information transferred by different stereoscopic cues. The inconsistencies have led human brains fall into confliction when they solve the stereoscopic cues, affecting the normal human visual system, making people feel uncomfortable, not to mention observing long duration.

The reason that the maximum intensity projection possesses such a problem is related to its own rendering principle, i.e., the maximum intensity projection rendering method is to display the object with maximum intensity in the line of sight. The maximum intensity projection principle does not consider the spatial relationships between objects, that is, it does not produce any meaningful spatial cues. On contrary, its results unwittingly violate an important stereoscopic cueing: the blocking relationship. There is often at least more than one object in a typical three-dimensional scene, which can be artificially distinguished. We cannot make any assumptions on their shapes and positions. The sight-points during the rendering usually are also random. In the projection results, the object with maximum intensity will always cover up other objects with relatively less intensity, regardless of its position relative to the sight-point is at before or after the less dense objects. Furthermore, since an observer only obtains the spatial information of a digital three-dimensional data from the two-dimensional projection images, the observer, in a maximum intensity projection case, will always recon that the object with maximum intensity is relatively closer to the observer than the objects of less intensity. This is inconsistent with the fact that in real scene the maximum intensity object is located further away from the sight-point than some of the lower intensity objects. This inconsistency, in the conventional three-dimensional display mode, is not a problem, but in the stereoscopic display mode, will cause confliction with parallax, another very important stereoscopic cue. Because the parallax is always calculated according to the real spatial positions of objects, it can be believed that the parallax maintains consistency with the original three-dimensional digital data. So, the maximum intensity projection will encounter stereoscopic cueing confliction in stereoscopic display mode.

In order to make the maximum intensity projection to provide more spatial information, some modified algorithms have been proposed. The most typical proposal is the addition of depth information, such as depth cueing or depth weight, etc. W. Heidrich, M. McCool and J. Steens proposed the depth cueing method in their publication, "Interactive Maximum Projection Volume Rendering" (Proceedings visualization, 1995). The method, before comparing the maximum sampling points, perform a weighting calculation to sampling points according to the distances of the points from the sight-point, say that the further away a sampling point from the sight point, the smaller the weighting factor is for the sampling point. This way, the influence of the remote objects is weakened. By adjusting the distance weighting factors, though an object in a particular distance can be focused on, it does not completely solve the problem, because the weighted maximum sampling point may still be the initial maximum sampling point, and furthermore, the comparison method for the maxima is of discrete nature which may lose a lot of meaningful spatial information.

Sato Y., Shiraga N., Nakajima S., Tamura S. and Kikini s R. proposed the concept of local maximum intensity projection (LMIP) in their paper, "Local Maximum Intensity Projection (LMIP): A New Rendering Method for Vascular Visualization" (Journal of Computer Assisted Tomography, Vol. 22, No. 6, pp. 912 917, 1998). The proposal suggests to render the first local maximum intensity point in the line of sight, which is the first object encountered by the sight. LMIP method also uses a threshold, any object smaller than which is regarded as background. LMIP is helpful in reducing the probability of blocking nearer but less intensive objects by the farther but more intensive objects in the depth cueing method, however, still cannot solve the problem completely.

On the basis of the above mentioned background, the present invention proposes a method to solve the three-dimensional cueing confliction problem of maximum intensity projection in the stereoscopic display mode.

SUMMARY

The present invention proposes an image display method and an image display apparatus to solve the three-dimensional cueing confliction problem of maximum intensity projection in the stereoscopic display mode. In accordance with the present invention, a three-dimensional surface which has equal distance to a sight-point is utilized as a reference surface, and the distances from all of the local maximum intensity points to this reference surface are calculated, then, the weighting factor of each local maximum intensity point is calculated according to the distances and predetermined weighting function, afterwards, the values of local maximum intensity points are adjusted according to the obtained weighting factors, and finally, the maximum intensity projection value is produced by synthesizing all of the adjusted values of local maximum intensity points.

According to the first aspect of the present invention, an image processing apparatus comprises: a local maximum intensity points determining unit, a local maximum intensity points weighting unit and a local maximum intensity points synthesizing unit. For each pixel on the projection image of the first sight-point, the local maximum intensity points determining unit finds out all local maximum intensity points from the three-dimensional data along the line of sight determined by the first sight-point and each pixel; the local maximum intensity points weighting unit, for each local maximum intensity point, calculates the distance from the local maximum intensity point to the reference surface, then, the intensity value of the local maximum point is weighted according to the calculated distance and the distance weighting function, so that the weighted intensity value of the local maximum intensity point is obtained; the local maximum intensity points synthesizing unit selects the maximum value out of the weighted intensity values of all local maximum intensity points as the data of the pixel on the projection image of the first sight-point.

Preferably, the reference surface is an isometric surface formed of equidistant points from the first sight-point.

Preferably, for each pixel on the projection image of the second sight-point, the local maximum intensity points determining unit finds out all local maximum intensity points from the three-dimensional data along the line of sight determined by the second sight-point and each pixel; the local maximum intensity points weighting unit, for each local maximum intensity point, calculates the distance from the local maximum intensity point to the reference surface, then, the intensity value of the local maximum point is weighted according to the calculated distance and the distance weighting function, so that the weighted intensity value of the local maximum intensity point is obtained; the local maximum intensity points synthesizing unit selects the maximum value out of the weighted intensity values of all local maximum intensity points as the data of the pixel on the projection image of the second sight-point.

Preferably, the image processing apparatus further comprises:
a display unit, which is used to display alternately or simultaneously the first sight-point projection image and the second sight-point projection image.

Preferably, the reference surface is an isometric surface formed of equidistant points from the middle point of the first sight-point and the second sight-point.

Preferably, the distance weighting function is a kind of function attributing heavier weighting factors to the local maximum intensity points which are close to the reference surface. More preferably, the distance weighting function is a Gaussian function, a cosine function, or a triangular function, where the distance is the independent variable while the weighting factor is the dependent variable.

Preferably, the maximum value from all of the weighted intensity values of the local maximum points is selected as the data for the pixel on the projection image of the first sight-point/the projection image of the second sight-point, the local maximum intensity points synthesizing unit synthesizes the weighted intensity values of all local maximum intensity points in accordance with the synthesizing function to produce the data for the pixel on the projection image of the first sight-point/the projection image of the second sight-point.

More preferably, the synthesizing function is an additive function, i.e. by adding all weighted intensity values of the local maximum intensity points, the result of the addition is taken as the data for the pixel on the projection image of the first sight-point/the projection image of the second sight-point.

More preferably, the synthesizing function is a transparency blending function, i.e. the weighted intensity values of all local maximum points are synthesized by utilizing a blending method in accordance with transparency from front to rear, and the result of the synthesis is taken as the data for the pixel on the projection image of the first sight-point/the projection image of the second sight-point.

According to the second aspect of the present invention, an image processing method comprises: for each pixel on the projection image of the first sight-point, all local maximum intensity points are found out from the three-dimensional data along the line of sight determined by the first sight-point and each pixel; for each local maximum intensity point, the distance from the local maximum intensity point to the reference surface is calculated, and the intensity value of the local maximum point is weighted according to the calculated distance and the distance weighting function, so that the weighted intensity value of the local maximum intensity point is obtained; the maximum value out of the weighted intensity values of all local maximum intensity points is selected as the data of the pixel on the projection image of the first sight-point.

Preferably, the reference surface is an isometric surface formed of equidistant points from the first sight-point.

Preferably, the image processing method further comprises: for each pixel on the projection image of the second sight-point, all local maximum intensity points are found out from the three-dimensional data along the line of sight determined by the second sight-point and each pixel; for each local maximum intensity point, the distance from the local maximum intensity point to the reference surface is calculated, and the intensity value of the local maximum point is weighted according to the calculated distance and the distance weighting function, so that the weighted intensity value of the local maximum intensity point is obtained; the maximum value out of the weighted intensity values of all local maximum intensity points is selected as the data of the pixel on the projection image of the second sight-point.

Preferably, the first sight-point projection image and the second sight-point projection image are alternately or simultaneously displayed.

Preferably, the reference surface is an isometric surface formed of equidistant points from the middle point of the first sight-point and the second sight-point.

Preferably, the distance weighting function is a kind of function attributing heavier weighting factors to the local maximum intensity points which are close to the reference surface. More preferably, the distance weighting function is a Gaussian function, a cosine function, or a triangular function, where the distance is the independent variable while the weighting factor is the dependent variable.

Preferably, the maximum value from all of the weighted intensity values of the local maximum points is selected as the data for the pixel on the projection image of the first sight-point/the projection image of the second sight-point, and the data for the pixel on the projection image of the first sight-point/the projection image of the second sight-point is produced by synthesizing the weighted intensity values of all local maximum intensity points in accordance with the synthesizing function.

More preferably, the synthesizing function is an additive function, i.e. by adding all weighted intensity values of the local maximum intensity points, the result of the addition is taken as the data for the pixel on the projection image of the first sight-point/the projection image of the second sight-point.

More preferably, the synthesizing function is a transparency blending function, i.e. the weighted intensity values of all local maximum points are synthesized by utilizing a blending method in accordance with transparency from front to rear, and the result of the synthesis is taken as the data for the pixel on the projection image of the first sight-point/the projection image of the second sight-point.

BRIEF DESCRIPTION OF THE DRAWINGS

With the following description, accompanied by the following figures, on preferred exemplary embodiments, the above mentioned and other objectives, characteristics, and advantages of the present invention shall become further cleared, wherein.

DETAILED DESCRIPTION

Preferred exemplary embodiments of the present invention are described in detail below with reference figures. Some minutiae and functions, which are not essential to the present invention, are omitted during the description, in order to prevent confusion in understanding of the present invention.

The present invention provides an image display method and an image display apparatus, which solve the three-dimensional cueing confliction problem of the maximum intensity projection in the stereoscopic display, while enabling users to select and render with emphasis the maximum intensity projection of the objects of interest, so that to realize the stereoscopic display.

Figure 1:
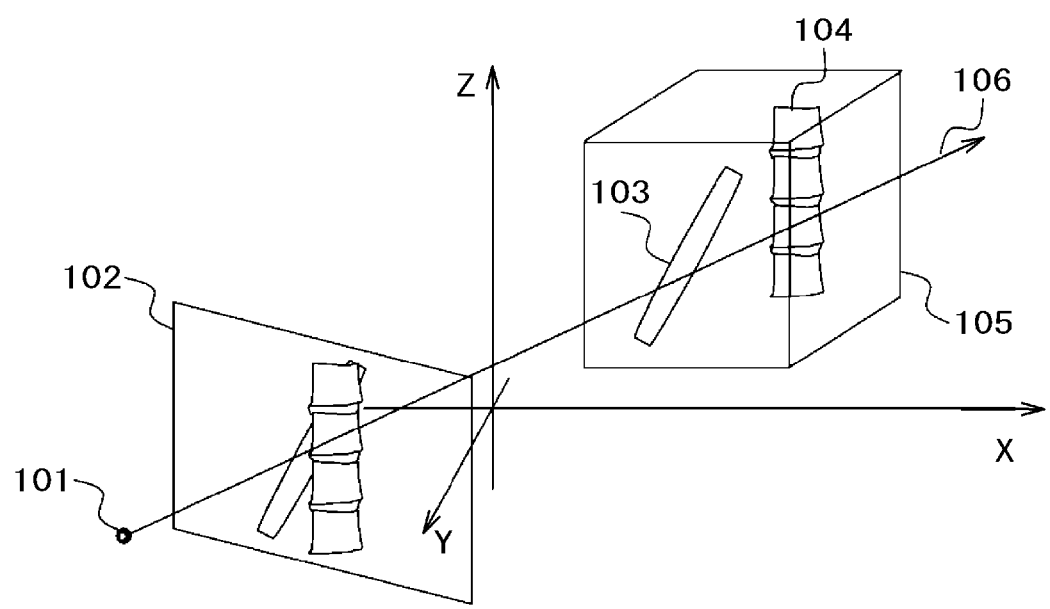
FIG. 1 is the simplified model of a three-dimensional CT imaging data of a human head and neck area, in which the two major human tissues, the cervical and carotid arteries, are shown.

FIG. 1 is the simplified model of three-dimensional CT angiography data of a human head and neck area.

In FIG. 1, the two major human tissues, cervical vertebra 104 and carotid artery 103, are shown. Sight line 106 is a ray emitted from sight-point 101 and penetrating through a three-dimensional volume data 105. Medical data are generally present complex human tissues with intensities. From the image viewpoint, an intensity corresponds to a specific gray scale value, therefore, the intensity here is equivalent to the visually seen gray scale. As the bone tissue has a high intensity, the bone tissue has very high gray scale in the CT imaging data. The intensity of blood vessels in angiography is low, and intensities of other soft tissues are even further lower. So, in this simplified model, the other soft tissues are classified as the background. The conventional maximum intensity projection algorithm selects sampling point having a maximum intensity on the line of sight, and issue the intensity value of the point to the pixel on the corresponding projection plane. As results, in the final maximum intensity projection image 102, some area of the blood vessels, which are closer to the sight-point, is blocked by the cervical vertebra, which is farther to the sight-point. Therefore, the spatial relationship of the tissues, i.e., the depth information in the direction of the line of sight, cannot be determined by the conventional maximum intensity projection and the blocking relationship.

Figure 2:
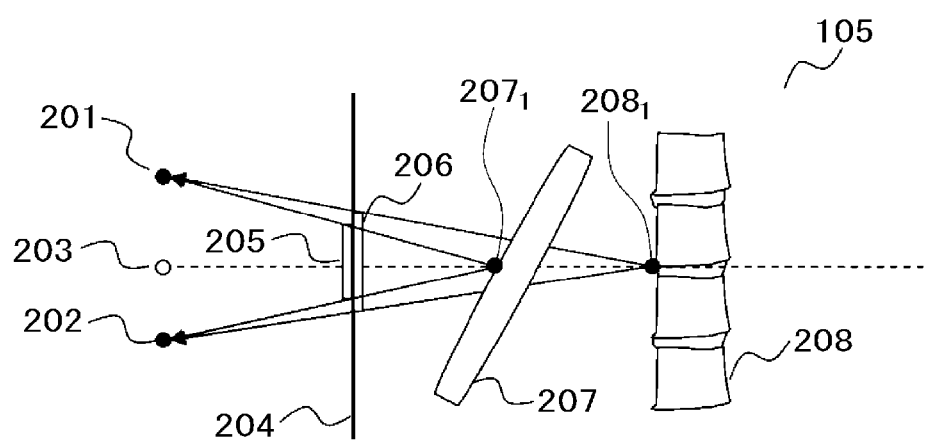
FIG. 2 is a schematic diagram used for explaining the stereoscopic maximum intensity projection. The stereoscopic projection is a computer simulation of human visual system. Contrary to the conventional three-dimensional rendering system, the stereoscopic projection system consists of left and right dual eye-sights. By rendering two images of three-dimensional data, the images for left and right eye-sights, and passing them through the stereoscopic display device to the left and right eyes of a human, the stereoscopic projection system shall make the user feel more realistic and immersive stereoscopic effects. Here, parallax, an important three-dimensional cue to be used in stereoscopic rendering, is highlighted.

FIG. 2 is a schematic diagram used for explaining the stereoscopic maximum intensity projection. The major difference between the stereoscopic projection method and the traditional three-dimensional projection method is the latter added a sight-point, so that added a new three-dimensional cue, the parallax, through two sight-points. Sight-point 203 is the location of a conventional single sigh-point, for instance, sight-point 101 in FIG. 1, in the traditional three-dimensional projection model. Left sight-point 201 and right sight-point 202 are symmetrically distributed at the two sides of the single sight-point 203. Projecting from the two sight-points 201 and 202 will result in the left and right two images of the stereoscopic three-dimensional rendering. In the stereoscopic projection mode, each spatial point of three-dimensional data has two projection points on projection screen 204, corresponding to left sight-point 201 and right sight-point 202. The distance between the two projection points is called as parallax, for instance, the parallax of point 207 on blood vessel 207 on projection screen 204 is represented by coverage range 205, and the parallax of point 208 on neck 208 on projection screen 204 is represented by coverage range 206. The size of the parallax is determined by the distances among the three-dimensional spatial point, sight-point 203, and projection screen 204: in the case of fixed projection screen 204, the farther away the object from the sight-point 203, the greater the parallax is, and vice versa. Therefore, the size of the parallax indirectly reflects the distance of the object from sight-point 203. The human visual system automatically obtains the information two images from the left and right images, for sensing the distance of different objects. The parallax is a three-dimensional cue in stereoscopic three-dimensional rendering technology, and the blocking relationship of objects is another important three-dimensional cue. When the three-dimensional cues are consistent in the rendering results, they can enhance each other for more realistic stereoscopic three-dimensional effects; but if there are some conflictions between them, then the three-dimensional effect will diminish, or even affect the human visual system. The present invention proposes to eliminate as much as possible the three-dimensional cue confliction problem in the stereoscopic maximum intensity projection by weakening even eliminating the blocking relationship cues.

Figure 3:
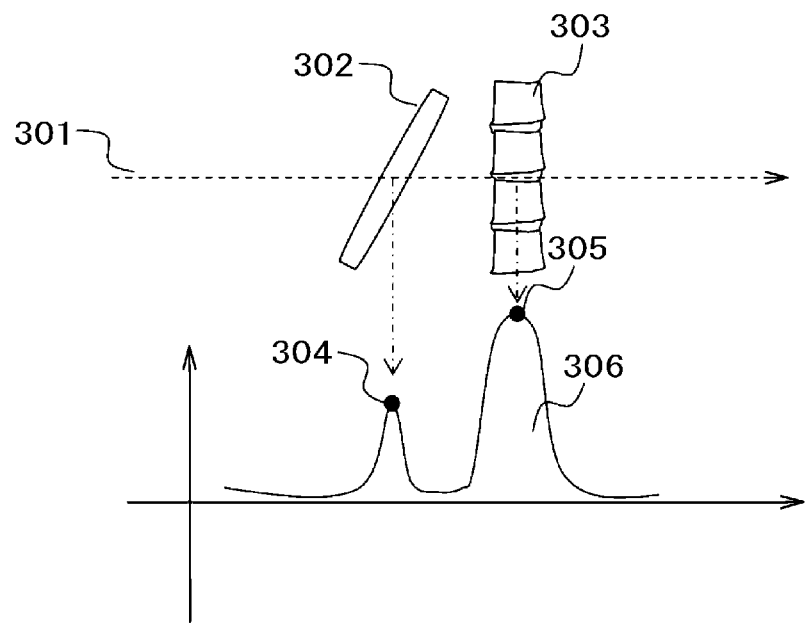
FIG. 3 is a schematic diagram used for explaining the concept and effect of a local maximum intensity point. The local maximum intensity point is helpful in eliminating the cueing confliction of three-dimensional data in the stereoscopic maximum intensity projection.

FIG. 3 is a schematic diagram used for explaining the local maximum intensity value.

A local maximum intensity value is a value with respect to the global maximum intensity value, in other words, the global maximum intensity value is the maximum intensity value of all sampling points within the scope of the three-dimensional data through which the line of sight is penetrating, while the local maximum intensity value is the maximum intensity value of sampling points within the scope of a single tissue through which the line of sight is penetrating. In FIG. 3, line of sight 301 is penetrating through blood vessel 302 and cervical vertebra 303. Utilizing a two dimensional coordinate system to present the intensity variation of the sampling points along line of sight 201, the horizontal axis represent the direction of the line of sight, and the vertical axis represents the intensity values of the sampling points; graph 306 is rendered with the values of the sampling points on the line of sight; local maximum intensity value 304 represents the maximum intensity point of blood vessel 302 on line of sight 301; similarly, local maximum intensity value 305 represents the maximum intensity point of cervical vertebra 303 on line of sight 301. Compared to the global maximum intensity value, the local maximum intensity projection value can provide more information about a single tissue, so that the human eyes can distinguish different tissues through the local maximum intensity values in the line of sight, which in turn provides the necessary preparation for the stereoscopic maximum intensity projection.

Figure 4:
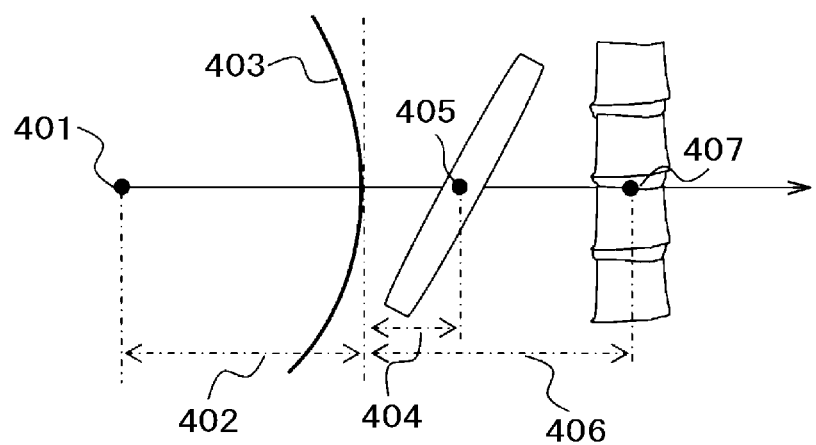
FIG. 4 is a schematic diagram used for explaining how to realize the stereoscopic maximum intensity projection by utilizing the local maximum intensity value, and how to avoid the three-dimensional cueing confliction.

FIG. 4 describes how to use the local maximum intensity value to achieve the stereoscopic maximum intensity projection. Local maximum intensity point 405 and 407 are two local maximum intensity points on the line of sight emitted from sight-point 401. In the present invention, it is assumed that there is a surface, all points on which are equidistant from the sight-point, called equidistant surface (spherical surface). As shown in FIG. 4, equidistant surface 403 is a spherical surface formed by all points with equal distance to sight-point 401, all points of the spherical surface, where, distance 402 is the distance between equidistant surface 403 and the sight-point 401. Since the intensity value of local maximum intensity point 405 is less than the intensity value of local maximum intensity point 407, in the traditional maximum intensity projection, the intensity value of local maximum intensity point 407 will be used as the final result of the projection, which results in the local maximum intensity point 405 being blocked. To avoid this as much as possible, a weighting factor calculated according to the depth information is assigned to each local maximum intensity value. By assigning a greater weighting factor to a local maximum intensity value of a sampling point closer to the sight-point, the sampling point is not blocked by the objects with greater intensity but actually located behind. The simplest way is to directly use the distance between the sight-point and the local maximum intensity point to calculate the weighting factor. However, the disadvantage of this approach is that the user cannot easily select objects of interest. Although the method of the transfer function can map the depth to particular weighting values, but because the setting of the transfer function may rather be cumbersome, this is also not productive way for the user to quickly find the object of interest. In the present invention, the equidistant surface is set as the reference surface, the distances from the local maximum intensity point to the reference surface (refer to 404 and 406 in FIG. 4) are selected for the weighting factor calculation, where, the local maximum intensity point with smaller distance is given greater weighting value. Since the user can easily change the location of the equidistant surface (the reference surface), the objects nearby the equidistant surface (the reference surface) can easily be focused. Furthermore, preferably, the weighted intensity values of all local maximum points can be synthesized according to some preset synthesizing function, and the synthesis results are selected as the final result of the projection instead of simply selecting the global (weighted) maximum intensity value as the final projection result, to provide more spatial information. In the present description, although the equidistant surface is selected as the reference surface, but the present invention is not limited to it, one can select other suitable flat or curved surface as reference surface.

Figure 5A:
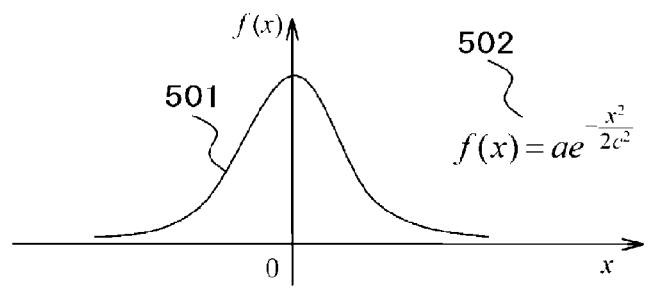
FIGS. 5A, 5B and 5C illustrate examples of weighting function, which are used for adjusting the local maximum intensity values, and take the distance from a local maximum point to the reference surface as the independent variable.
Figure 5B:
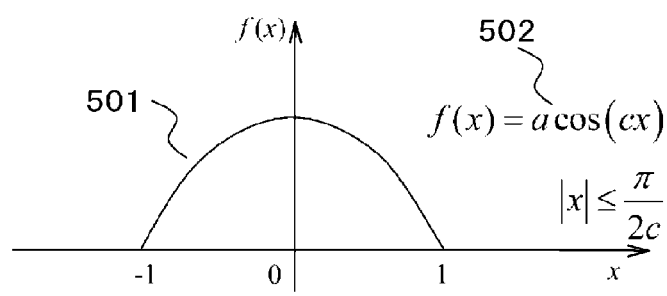
Figure 5C:
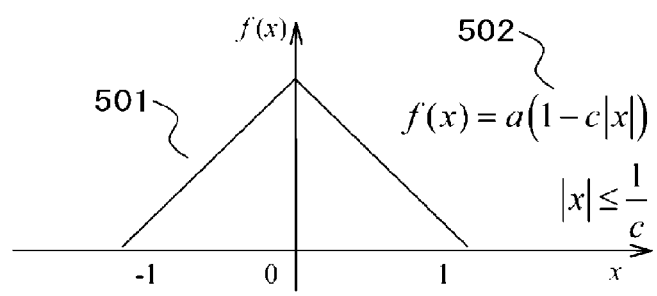

FIGS. 5A, 5B and 5C illustrate examples of weighting function, which are used for adjusting the local maximum intensity values, the horizontal axis of the two-dimensional coordinates represents the distance x of local maximum intensity points to the equidistant surface, the vertical coordinate represents the weighting factor f(x) with respect to the distance x.

FIG. 5A shows a Gaussian function $$f(x) = ae^{-\frac{x^2}{2c^2}},$$

wherein the parameters a and c are greater than 0 and can be set according to actual needs, which determine the height and half height of the Gaussian function. Since the Gaussian function is very natural and smooth, so the results after weighting can promote with emphasis the objects near the equidistant surface, while providing consideration to the local maximum intensity points in some distances.

FIG. 5B is a cosine function $$f(x) = a\cos(x) \ |x| \le \frac{\pi}{2c},$$

wherein the parameters a and c are greater than 0 and can be set according to actual needs, which determine the height and width of the cosine function.

FIG. 5C is a triangle function $$f(x) = a(1 - c|x|) \ |x| \le \frac{1}{c},$$

wherein the parameters a and c are greater than 0 and can be set according to actual needs, which determine the height and width of the triangle function.

After weighting each intensity value for all local maximum intensity points, the global maximum intensity value can simply be selected as the final projection result, or according to the preferred exemplary embodiments, all weighted local maximum intensity values can be added (simple additive synthesis), and the sum of the addition can be considered as the final result of the projection, or all weighted local maximum intensity values are synthesized by utilizing a blending method in accordance with transparency from front to rear, and the result of the synthesis is taken as the result of the projection.

Figure 6:
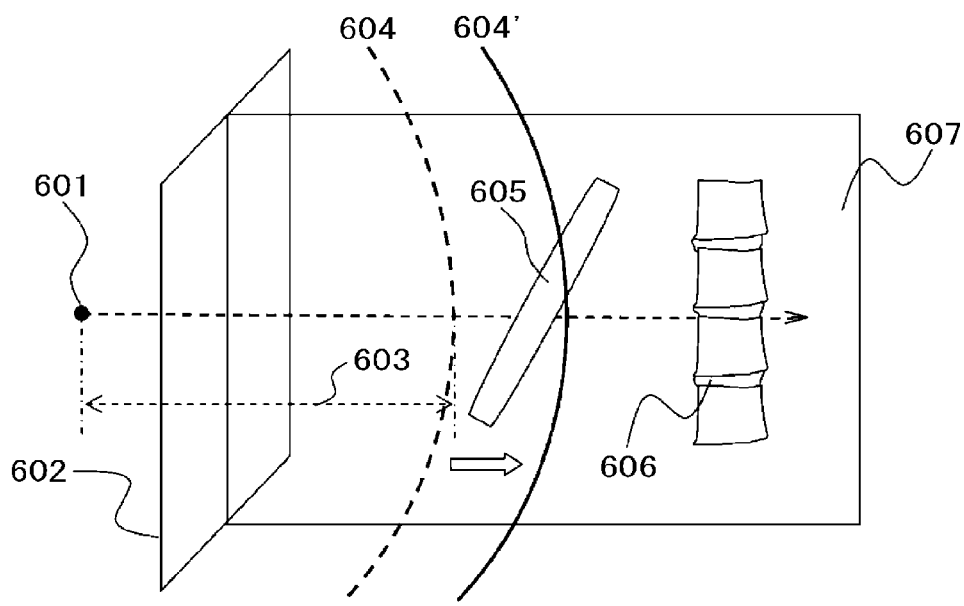
FIG. 6 is a schematic diagram used for explaining how the equidistant surface (the reference surface) is selected and its location is adjusted by making use of the information of a cross-section which is perpendicular to the main rendering plane and located inside the three-dimensional data.

FIG. 6 is a schematic diagram for explaining how to select and adjust the position of equidistant surface 604.

As defined in reference FIG. 4, the equidistant surface is a three-dimensional surface with the same distance to the sight-point in the three-dimensional data space. In strict sense, the equidistant surface is sphere 604 with sight-point 601 as its center and distance 603 as its radius. In order to enable the user to quickly select the object of interest on the line of sight, the present invention provides cross-section 607, which is parallel to the line of sight and perpendicular to maximum intensity projection screen 602. Cross-section 607 shows the information of three-dimensional data in the direction parallel to the line of sight, i.e., the depth information of the three-dimensional spatial data. The user can visually see different human tissues in the depth direction as well as the spatial distribution of equidistant surface 604. In this way, the user can easily modify the position of equidistant surface 604 (for example, from 604 moves to the 604'), so that greater weighting factors can be set for the objects of interest (for example, cervical vertebra 605 and carotid artery 606).

Figure 7:
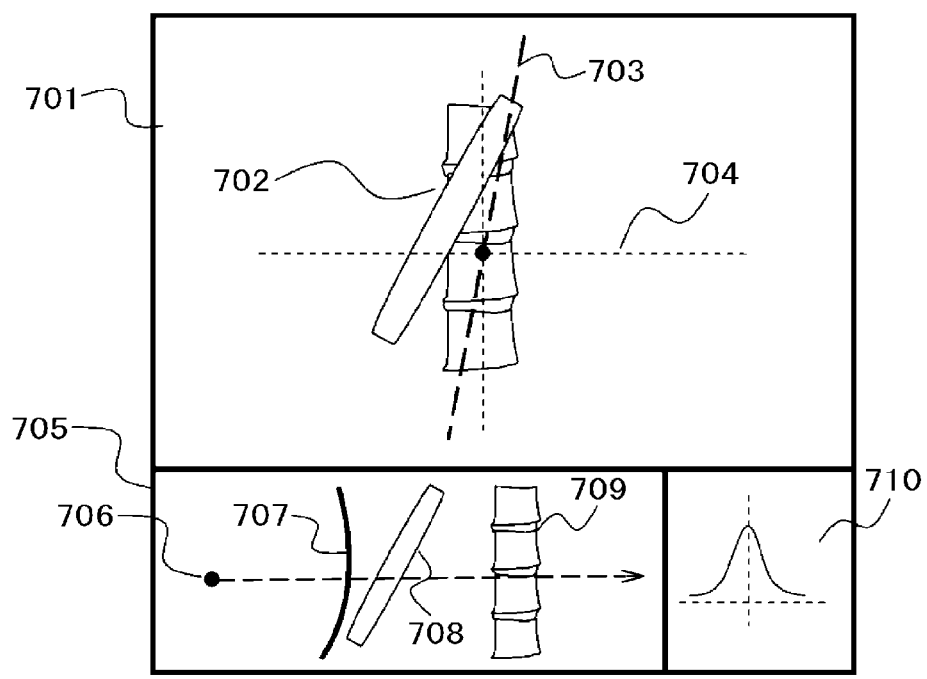
FIG. 7 shows the user interface diagram of the stereoscopic maximum intensity projection system of the present invention.

FIG. 7 shows the user interface of the stereoscopic maximum intensity projection system in the present invention.

Main view 701 is the main projection plane of the stereoscopic maximum intensity projection, while auxiliary view 705 is the cross-sectional view perpendicular to projection plane 701. In stereoscopic maximum intensity projection plane 701, mark 704 is a two-dimensional coordinate system used to position section view 705, mark 703 is a line segment with the origin of two-dimensional positioning coordinate system 704 as its middle point, which is the intersecting line between maximum intensity projection plane 701 and section view 705, called section selection line 703. The user can move two-dimensional positioning coordinate system 704 and section selection line 703 to adjust the position of section view 705. In section view 705, mark 707 is the intersecting line between the equidistant surface and section view 705, called equidistant line 707, mark 706 represents a sight-point. The user can move the position of equidistant line 707 inside section view 705 to modify the position of the equidistant surface in the three-dimensional space, and the system will calculate distances between all local maximum intensity points (e.g., the intersection between carotid artery 708 and cervical vertebra 709 and the line of sight) and the equidistant surface according to the position of the equidistant surface, calculate weighting factor for each local maximum point according to the calculated distance, and finally produce final projection image 702 through the synthesizing function. In projection image 702, the blood vessels (carotid artery 708) and the bone (cervical vertebra 709) presents a mixing effect, there is no blocking relationship of each other. Window 710 is used to select and adjust the weighting function, in which, the distance is the independent variable, and the weighting factor is the dependent variable. In window 710, the variation factors between the distance and the weighting factors can be adjusted (e.g., the parameters a and c in FIGS. 5A, 5B and 5C). The stereoscopic maximum intensity projection display system renders the left and right eye-sight images alternately and display them in the main screen view 701 to generate the disparity information (making use of the delay characteristics of human eyes, the user will see the stereoscopic image display). Because the blocking relationship between carotid artery 708 and cervical vertebra 709 has been weakened or even eliminated, the potential confliction problem of the three-dimensional cues are avoided.

Figure 8A:
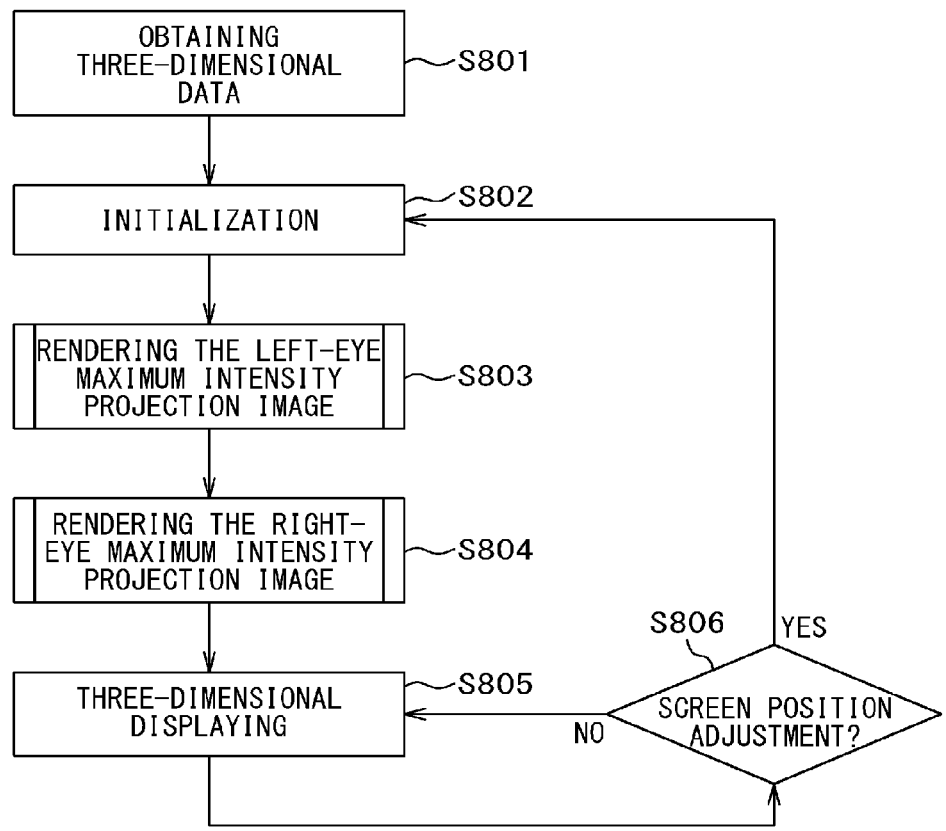
FIG. 8A shows the operation flow chart of the stereoscopic maximum intensity projection system of the present invention.

FIG. 8A is a schematic diagram showing the operational flow chart of the stereoscopic maximum intensity projection system of the present invention.

First, in step S801, obtain three-dimensional data, such as the regular three-dimensional CT tomography data.

Then, in step S802, initialize the position of the two sight-points in the three-dimensional model for the stereoscopic three-dimensional projection, simultaneously, initialize the positions of the section view and the equidistant surface, and the distance weighting function, for subsequent rendering the first screen image of the stereoscopic maximum intensity projection.

Next, in step S803, select the left sight-point and render the left eye-sight image; in step S804, select the right sight-point and render the right eye-sight image. Step S803 and step S804 are interchangeable, or may be executed in parallel.

Finally, in step S805, alternately or simultaneously display the two images (left eye-sight image and the right eye-sight image) to the user through the stereoscopic display device, to achieve stereoscopic display.

If the user, after seeing the stereoscopic display, wish to adjust the screen position to find the objects of interest, the process proceeds to step S806. The user can adjust the positions of the sight-point (for instance, sight-point 706 in FIG. 7) and the section view screen (for instance, window 705 in FIG. 7) utilizing the section selection line (for instance, coordinate system 704 and line 703 in FIG. 7) in the main projection window (for instance, window 701 in FIG. 7). Further on, the user can modify the position of the equidistant surface in the section view screen (for instance, window 705 FIG. 7), to make the objects of interest have greater weighting factors for fast positioning of them. The adjustment of all above parameters, such as sight-point, section selection line and the equidistant surface, can be done individually one or two or simultaneously two or all.

Figure 8B:
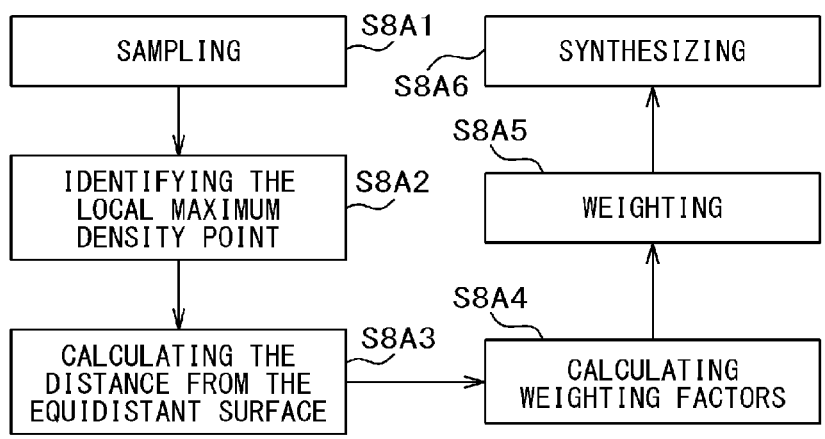
FIG. 8B shows the operation flow chart of single eye-sight image rendering (left eye-sight image or right eye-sight image)

FIG. 8B shows the operational flowchart a single eye-sight image (left eye-sight image or right eye-sight image) rendering.

For each pixel on the projection screen, do the following operation to get the whole screen of single eye-sight image.

In step S8A1, sample in equal intervals from the three-dimensional data along the line of sight determined by the sight-point and the pixel.

In step S8A2, find all local maximum intensity points from the sampled points.

In step S8A3, for each local maximum intensity point, calculate the distance from the local maximum intensity point to the equidistant surface.

In step S8A4, calculate the weighting factor for each local maximum intensity point according to the distance from the local maximum intensity point to the equidistant surface and in accordance with the distance weighting function.

In step S8A5, obtain the weighted intensity value for each local maximum intensity point by adjusting the intensity value of the local maximum intensity point according to the weighting factor of the local maximum intensity point.

In step S8A6, in accordance with the synthesizing function, synthesize all the weighted intensity values of the local maximum intensity points to obtain the final projection result as the pixel data of the projection screen.

Figure 9:
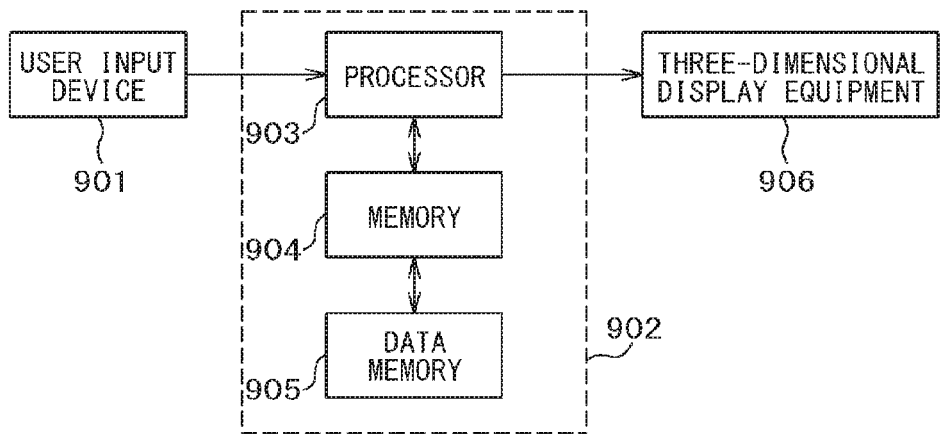
FIG. 9 shows the hardware configuration diagram of the stereoscopic maximum intensity projection system of the present invention.

FIG. 9 shows the hardware configuration diagram of the stereoscopic maximum intensity projection system of the present invention.

Computer 902 is a general purpose computer, mainly formed of processor unit 903, memory unit 904 and data storage unit 905. User input device 901 and stereoscopic display device 906 will work together with computer 902 to fulfill the user interaction tasks. The main function of stereoscopic display device 906 is to display alternately or simultaneously the left eye-sight and right eye-sight two images, and to ensure the user's left and right eyes receives left and right eye-sight images respectively. Processor 903 and memory device 904 complete the data processing according to the user interaction.

Figure 10:
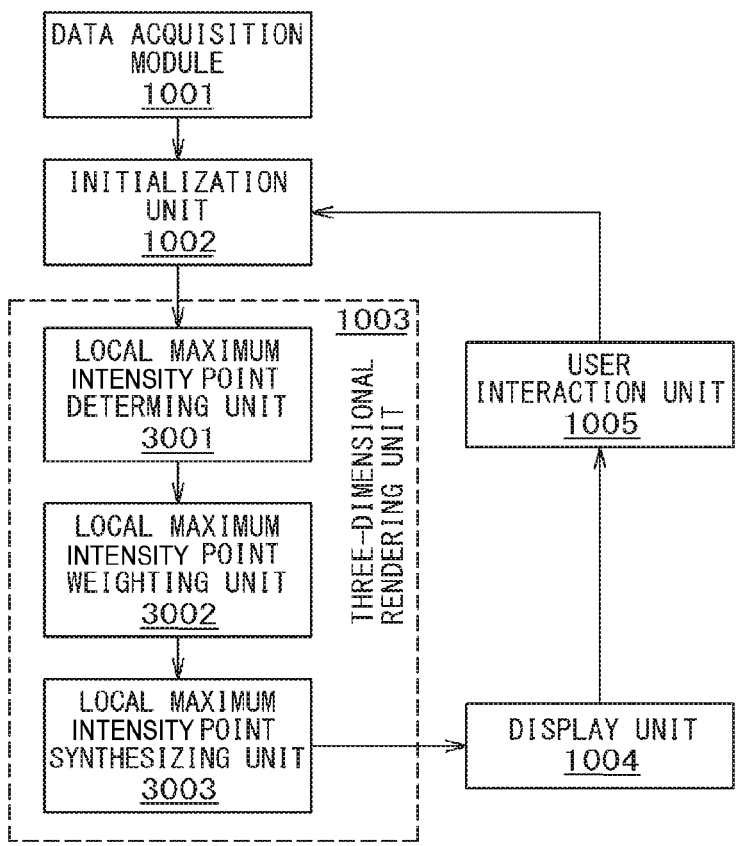
FIG. 10 shows more detailed hardware configuration diagram of the stereoscopic maximum intensity projection system the present invention.

FIG. 10 shows more detailed hardware configuration of the stereoscopic maximum intensity projection system of the present invention.

Data acquisition unit 1001 is used for acquiring three-dimensional data, such as regular three-dimensional CT scan data. Initialization unit 1002 is used to initialize the position of the two sight-points in the three-dimensional model for the stereoscopic three-dimensional projection, simultaneously, to initialize the positions of the section view and the equidistant surface, and the distance weighting function, for subsequent rendering the first screen image of the stereoscopic maximum intensity projection. Stereoscopic rendering unit 1003 is used to perform stereoscopic rendering operations, that is, to obtain respectively the left eye-sight image and the right eye-sight image data for each pixel according to the positions of the sight-point, the equidistant surface, and the distance weighting function. Stereoscopic rendering unit 1003 includes local maximum intensity point determining unit 3001, local maximum intensity point weighting unit 3002 and local maximum intensity point synthesizing unit 3003. For each pixel on the single eye-sight image (one of the left eye-sight image or the right eye-sight image), local maximum intensity point determining unit 3001 samples in equal intervals from the three-dimensional data along the line of sight determined by the sight-point and the pixel, and finds all local maximum intensity points from the sampled points; for each local maximum intensity point, local maximum intensity point weighting unit 3002 calculates the distance from the local maximum intensity point to the equidistant surface, and obtains the weighted intensity value for the local maximum intensity point by weighting the intensity value of the local maximum intensity point according to the calculated distance and the distance weighting function; local maximum intensity point synthesizing unit 3003 synthesizes all the weighted intensity values of the local maximum intensity points in accordance with the synthesizing function to obtain the final projection result as the pixel data on the single eye-sight image. Display unit 1004 is used for alternately or simultaneously displaying the two images (for instance, window 701 in FIG. 7) rendered by stereoscopic rendering unit 1003. In addition, display window 1004 also provides support for displaying the section view window (for instance, window 705 in FIG. 7) and weighting function window (for instance, window 710 in FIG. 7). User interaction unit 1005 provides the processing of user interaction, including allowing the user to select and adjust any one, two, or all three of the sight-point, section selection line, and the equidistant surface.

In the above description, for each step, various examples are listed. Although the inventor presented the instances associated with each other and marked accordingly, but this does not necessarily mean that there are definite corresponding relationship among these instances and marks. As long as there is no contradiction among the conditions of the selected instances, a technical plan or solution can be formed by selecting instances not corresponding the presented marks in different steps. Such a technical plan or solution should also be included in the scope of the present invention.

It should be noted that in the above description, the technical scheme or solution of the present invention are illustrated by way of showing examples. But, it does not mean that the present invention is limited to the above steps and unit structure. Wherever possible, the steps and unit structure may be adjusted and selected. Thus, some of the steps and the units are not necessarily the needed elements to implement the overall inventive concept of the present invention. Accordingly, the necessary technical characteristics of the present invention are limited only by the minimum requirements needed for implementation of the overall inventive concept of the present invention, and not limited by the detailed examples presented above.

The other configurations for the exemplary embodiments of the present invention disclosed here comprises the software program which executes steps and operations of the exemplary embodiments of the method outlined earlier and described in detail later. More specifically, the computer program product is an exemplary embodiment as follows: a computer readable medium, on which the computer program logic is encoded, when executed on a computing device, the computer program logic provides related operations, thereby providing the stereoscopic display solutions for three-dimensional data.

When executed on at least one processor of a computing system, the computer program logic causes the processor to execute the operations (methods) described in the exemplary embodiments of the present invention. This kind of configuration of the present invention is typically provided with a software, codes and/or other data structure set or encoded on media such as optical media (for instance, CD-ROM), floppy disks or hard disks, etc., which are computer readable media, or a firmware on chips of one or more ROMs or RAMs or PROMs, or other media of microcode, or application specific integrated circuit (ASIC), or downloadable software images and sharing database in one or more modules, etc. The software, the firmware, or such configuration can be installed on a computing device, so that one or more processors of the computing device execute the techniques described in the exemplary embodiments of the present invention. The operation of the software on devices such as combining a group of data communication devices or computing devices of other entities can also provide the system in accordance with the present invention. The system in accordance with the present invention can also be distributed across multiple software processes on multiple data communication devices, or in the software processes running on a group of small dedicated computers, or among all software processes running on a single computer.

It should be understood that, strictly speaking, the exemplary embodiments of the present invention can be implemented as software programs on a data communications device, software and hardware, or separate software and/or a separate circuit.

So far, the present invention has been described with the preferred exemplary embodiments. It should be understood that the technical workers in this field may perform various changes, substitutions, and additions without departing from the spirit and scope of the present invention. Therefore, the scope of the present invention is not limited to the above specific exemplary embodiments, but is defined by the appended claims.

What is claimed is:

1. An image processing apparatus comprising:
a memory; and
a processor coupled to the memory, and the memory stores instructions that, when executed by the processor, cause the processor to:
for each pixel on a projection image of a first sight-point:
calculate all first local maximum intensity points from three-dimensional data along a line of sight determined by the first sight-point and the respective pixel,
for each of the first local maximum intensity points, calculate a distance from the respective local maximum intensity point to a reference surface and then weight an intensity value of the respective local maximum intensity point according to the calculated distance and a distance weighting function, to obtain weighted intensity values of each of the first local maximum intensity points, and
select a maximum value out of the weighted intensity values of all the first local maximum intensity points as the data of the respective pixel of the projection image of the first sight-point; and
for each pixel of a projection image of a second sight-point:
calculate all second local maximum intensity points from the three-dimensional data along a line of sight determined by the second sight-point and the respective pixel,
for each of the second local maximum intensity points, calculate a distance from the respective second local maximum intensity point to the reference surface and then weight an intensity value of the respective second local maximum intensity point according to the calculated distance and the distance weighting function, to obtain weighted intensity values of each of the second local maximum intensity points, and
select a maximum value out of the weighted intensity values of all the second local maximum intensity points as the data of the respective pixel of the projection image of the second sight-point; and
display the projection image of the first sight-point from the three-dimensional data, as modified with the selected data for each respective pixel of the projection image of the first sight-point, and the projection image of the second sight-point from the three-dimensional data, as modified with the selected data for each respective pixel of the projection image of the second sight-point, wherein the reference surface is an isometric surface consisting of equidistant points from a middle point of the first sight-point and the second sight-point.

2. The image processing apparatus according to claim 1, further comprising:

a display unit to display alternately or simultaneously the projection image of the first sight-point and the projection image of the second sight-point.

3. The image processing apparatus according to claim 1, wherein the distance weighting function attributes heavier weighting factors to the first local maximum intensity points which are closer to the reference surface.

4. The image processing apparatus according to claim 3, wherein the distance weighting function is a Gaussian function, a cosine function, or a triangle function, where the distance is an independent variable and the weighting factor is a dependent variable.

5. The image processing apparatus according to claim 1, wherein the memory stores instructions that, when executed by the processor, cause the processor to: synthesize the weighted intensity values of all the first local maximum intensity points in accordance with a synthesizing function to produce the data for the respective pixel of the projection image of the first sight-point.

6. The image processing apparatus according to claim 5, wherein the synthesizing function is an additive function which adds all the weighted intensity values of the first local maximum intensity points, and the result of the addition is taken as the data for the respective pixel of the projection image of the first sight-point.

7. The image processing apparatus according to claim 5, wherein the synthesizing function is a transparency blending function where the weighted intensity values of all of the first local maximum intensity points are synthesized by a blending method in accordance with transparency from front to rear and the result of the synthesis is taken as the data for the respective pixel of the projection image of the first sight-point.

8. An image processing method, comprising:

for each pixel on a projection image of a first sight-point:

calculating all first local maximum intensity points from three-dimensional data along a line of sight determined by the first sight-point and the respective pixel, for each of the first local maximum intensity points, calculating a distance from the respective local maximum intensity point to a reference surface and then weighting an intensity value of the respective local maximum intensity point according to the calculated distance and a distance weighting function, to obtain weighted intensity values of each of the first local maximum intensity points, and selecting a maximum value out of the weighted intensity values of all the first local maximum intensity points as the data of the respective pixel of the projection image of the first sight-point;

for each pixel on a projection image of a second sight-point:

calculating all second local maximum intensity points from the three-dimensional data along a line of sight determined by the second sight-point and the respective pixel, for each of the second local maximum intensity points, calculating a distance from the respective second local maximum intensity point to the reference surface and then weighting an intensity value of the respective second local maximum intensity point according to the calculated distance and the distance weighting function, to obtain weighted intensity values of each of the second local maximum intensity points; and selecting a maximum value out of the weighted intensity values of all the second local maximum intensity points as the data of the respective pixel of the projection image of the second sight-point; and displaying the projection image of the first sight-point from the three-dimensional data, as modified with the selected data for each respective pixel of the projection image of the first sight-point, and the projection image of the second sight-point from the three-dimensional data, as modified with the selected data for each respective pixel of the projection image of the second sight-point, wherein the reference surface is an isometric surface consisting of equidistant points from a middle point of the first sight-point and the second sight-point.

9. The image processing method according to claim 8, further comprising:

alternately or simultaneously displaying the projection image of the first sight-point and the projection image of the second sight-point.

10. The image processing method according to claim 8, wherein the distance weighting function attributes heavier weighting factors to the first local maximum intensity points which are closer to the reference surface.

11. The image processing method according to claim 10, wherein the distance weighting function is a Gaussian function, a cosine function, or a triangle function, where the distance is an independent variable and the weighting factor is a dependent variable.

12. The image processing method according to claim 8, further comprising:

synthesizing the weighted intensity values of all the first local maximum intensity points in accordance with a synthesizing function to produce the data for the respective pixel of the projection image of the first sight-point.

13. The image processing method according to claim 12, wherein the synthesizing function is an additive function which adds all the weighted intensity values of the first local maximum intensity points, and the result of the addition is taken as the data for the respective pixel of the projection image of the first sight-point.

14. The image processing method according to claim 12, wherein the synthesizing function is a transparency blending function where the weighted intensity values of all of the first local maximum intensity points are synthesized by a blending method in accordance with transparency from front to rear, and the result of the synthesis is taken as the data for the respective pixel of the projection image of the first sight-point.

15. The image processing apparatus according to claim 1, wherein the reference surface is moved closer to or further from the middle point.

16. The image processing method according to claim 8, wherein the reference surface is moved closer to or further from the middle point.

* * * * *